United States Patent
Gavai et al.

(10) Patent No.: US 7,151,176 B2
(45) Date of Patent: Dec. 19, 2006

(54) PYRROLOTRIAZINE COMPOUNDS

(75) Inventors: Ashvinikumar V. Gavai, Princeton Junction, NJ (US); Wen-Ching Han, Newtown, PA (US); Yufen Zhao, Pennington, NJ (US); Ping Chen, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/253,832

(22) Filed: Oct. 19, 2005

(65) Prior Publication Data

US 2006/0089358 A1    Apr. 27, 2006

Related U.S. Application Data

(60) Provisional application No. 60/620,784, filed on Oct. 21, 2004.

(51) Int. Cl.
  C07D 487/04  (2006.01)
  A61K 31/53   (2006.01)
  A61P 19/02   (2006.01)
  A61P 35/00   (2006.01)

(52) U.S. Cl. ..................... 544/183; 514/243
(58) Field of Classification Search ............. 544/183; 514/243
  See application file for complete search history.

(56) References Cited

U.S. PATENT DOCUMENTS

| | | | |
|---|---|---|---|
| 5,787,545 | A  | 8/1998  | Colens |
| 6,867,300 | B1 | 3/2005  | Godfrey, Jr. et al. |
| 6,908,916 | B1 | 6/2005  | Mastalerz et al. |
| 6,916,815 | B1 | 7/2005  | Vite et al. |
| 6,933,386 | B1 | 8/2005  | Bhide et al. |
| 6,969,717 | B1 | 11/2005 | Bhide et al. |
| 6,982,265 | B1 | 1/2006  | Hunt et al. |
| 2003/0232831 | A1 | 12/2003 | Dyckman et al. |
| 2003/0232832 | A1 | 12/2003 | Lombardo et al. |
| 2004/0229877 | A1 | 11/2004 | Leftheris et al. |
| 2005/0197339 | A1 | 9/2005  | Gavai et al. |
| 2005/0209454 | A1 | 9/2005  | Swaminathan et al. |
| 2006/0004006 | A1 | 1/2006  | Brozilleri et al. |
| 2006/0009454 | A1 | 1/2006  | Cai et al. |
| 2006/0014745 | A1 | 1/2006  | Gavai et al. |

FOREIGN PATENT DOCUMENTS

| | | |
|---|---|---|
| EP | 0 713 876  | 5/1996 |
| WO | WO 98/08847 | 3/1998 |
| WO | WO 00/71129 | 11/2000 |
| WO | WO 02/40486 | 5/2002 |
| WO | WO 03/042172 | 5/2003 |
| WO | WO 03/090912 | 11/2003 |
| WO | WO 2004/009784 | 1/2004 |

OTHER PUBLICATIONS

Cecil Textbook of Medicine, edited by Bennet, J.C., and Plum F., 20th edition, vol. 1, 1004-1010, 1996.*
Mass, R. D., Int. J. Radiation Oncology Bio. Phys. vol. 58(3): 932-940, 2004.*
Fabbro et al. Pharmacology & therapeutics 93, 79-98, 2002.*
Ewald, H. et al., "Reaktionen von 1,2,4-Triazinen mit Acetylendicarbonsaure-dimethylester", Liebigs Ann. Chem., pp. 1718-1724 (1977).
Hunt, J.T. et al., "Discovery of the Pyrrolo[2,1-f][1,2,4]triazine Nucleus as a New Kinase Inhibitor Template", J. Med. Chem., vol. 47, No. 16, pp. 4054-4059 (2004).
Migliara, O. et al., "Synthesis of a New Bridgehead Nitrogen Heterocyclic System. Pyrrolo[2,1-*f*]-1,2,4-triazine Derivatives", J. Heterocyclic Chem., vol. 16, pp. 833-834 (1979).
Neunhoeffer, H. et al., "Cycloadditionen mit Methoxy- und dialkylamino-1,2,4-Triazinen", Liebigs Ann. Chem., pp. 1413-1420 (1977).
Patil, S.A. et al., "Synthesis of Pyrrolo[2,1-*f*][1,2,4]triazine Congeners of Nucleic Acid Purines via the *N*-Amination of 2-Substituted Pyrroles", J. Heterocyclic Chem., vol. 31, pp. 781-786 (1994).
Quintela, J.M. et al., "A Ready One-pot Preparation for Pyrrolo[2,1-*f*][1,2,4]triazine and Pyrazolo[5,1-*c*]pyrimido[4,5-*e*]triazine Derivatives", Tetrahedron, vol. 52, No. 8, pp. 3037-3048 (1996).

* cited by examiner

Primary Examiner—Venkataraman Balasubramanian
(74) Attorney, Agent, or Firm—Elliott Korsen

(57) ABSTRACT

The present invention provides compounds of formula I

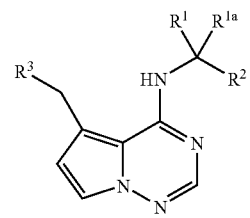

and pharmaceutically acceptable salts thereof.

The compounds of the invention inhibit tyrosine kinase activity of growth factor receptors such as HER1, HER2 and HER4 thereby making them useful as antiproliferative agents. The compounds are also useful for the treatment of other diseases associated with signal transduction pathways operating through growth factor receptors.

5 Claims, No Drawings

PYRROLOTRIAZINE COMPOUNDS

This application claims the benefit of U.S. Provisional Application No. 60/620,784, filed Oct. 21, 2004, incorporated herein by reference in its entirety.

BACKGROUND OF THE INVENTION

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain.

The human epidermal growth factor receptor (HER) family consists of four distinct receptor tyrosine kinases referred to HER1, HER2, HER3, and HER4. These kinases are also referred to as erbB1, erbB2, etc. HER1 is also commonly referred to as the epidermal growth factor (EGF) receptor. With the exception of HER3, these receptors have intrinsic protein kinase activity that is specific for tyrosine residues of phosphoacceptor proteins. The HER kinases are expressed in most epithelial cells as well as tumor cells of epithelial origin. They are also often expressed in tumor cells of mesenchymal origin such as sarcomas or rhabdomyosarcomas. RTKs such as HER1 and HER2 are involved in cell proliferation and are associated with diseases such as psoriasis and cancer. Disruption of signal transduction by inhibition of these kinases would have an antiproliferative and therapeutic effect.

The enzymatic activity of receptor tyrosine kinases can be stimulated by either overexpression, or by ligand-mediated dimerization. The formation of homodimers as well as heterodimers has been demonstrated for the HER receptor family. An example of homodimerization is the dimerization of HER1 (EGF receptor) by one of the EGF family of ligands (which includes EGF, transforming growth factor alpha, betacellulin, heparin-binding EGF, and epiregulin). Heterodimerization among the four HER receptor kinases can be promoted by binding to members of the heregulin (also referred to neuregulin) family of ligands. Such heterodimerization as involving HER2 and HER3, or a HER3/HER4 combination, results in a significant stimulation of the tyrosine kinase activity of the receptor dimers even though one of the receptors (HER3) is enzymatically inert. The kinase activity of HER2 has been shown to be activated also by virtue of overexpression of the receptor alone in a variety of cell types. Activation of receptor homodimers and heterodimers results in phosphorylation of tyrosine residues on the receptors and on other intracellular proteins. This is followed by the activation of intracellular signaling pathways such as those involving the microtubule associated protein kinase (MAP kinase) and the phosphatidylinositol 3-kinase (PI3 kinase). Activation of these pathways have been shown to lead to cell proliferation and the inhibition of apoptosis. Inhibition of HER kinase signaling has been shown to inhibit cell proliferation and survival.

Tropomysosin Related Kinases (Trk) are a family of receptor tyrosine kinases composed of three family members, TrkA, TrkB and TrkC. The Trks bind with high affinity and mediate the signal transduction of the Neurotrophin family of ligands whose prototype member is Nerve Growth Factor (NGF). In addition, a co-receptor lacking enzymatic activity, p75, has been identified which binds all NTs with low affinity and regulates neurotrophin signaling. A critical role of the Trks and their ligands during the development of the central and peripheral nervous systems have been established through gene disruption studies in mice. In particular, TrkA-NGF interaction was shown as a requirement for the survival of certain peripheral neuron populations involved in mediating pain signaling. In addition to these developmental consequences of Trk signaling, the subversion of this receptor and its signaling pathway in certain malignancies has also been documented. Of particular note are reports of activating chromosomal rearrangements of Trks in thyroid and breast cancers and receptor point mutations predicted to be constitutively activating in colon tumors. In addition to these activation mechanisms, elevated Trk receptor and ligand have also been reported in a variety of tumor types including multiple myeloma, melanoma, and pancreatic cancrcinoma. The oncogenic properties of Trk signaling in multiple tumor types makes the modulation of the Trk receptor signaling a potentially attractive therapeutic intervention point in different malignancies.

Other RTKs such as VEGFR-2 are associated with the proliferation of endothelial cells as well as tumor cells. Disruption of this pathway would have an antiproliferative effect and a therapeutic effect on disorders related to vasculogenesis or angiogenesis.

DETAILED DESCRIPTION OF THE INVENTION

The present invention provides for compounds of formula I, pharmaceutical compositions employing such compounds and methods of using such compounds.

In accordance with the present invention, compounds of formula I

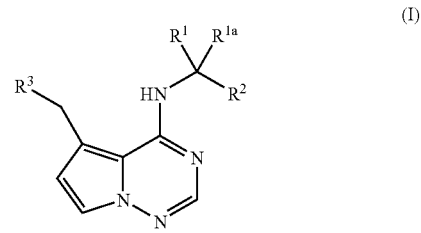

wherein the symbols have the following meanings and are, for each occurrence, independently selected:

$R^1$ and $R^{1a}$ are independently hydrogen, loweralkyl or phenyl;

$R^2$ is aryl, substituted aryl, heteroaryl or substituted heteroaryl; said substituents on the substituted aryl or substituted heteroaryl group are selected from the group consisting of one or more hydrogen, halogen, alkyl, substituted alkyl, alkoxy, substituted alkoxy, aryl, substituted aryl, aryloxy and, substituted aryloxy;

$R^3$ is heterocyclyl or substituted heterocyclyl, said substituents on the substituted heterocyclyl group are selected from the group consisting of one or more hydrogen, halogen, —OH, alkyl, substituted alkyl, —CN, —NH$_2$, —CONHR, —OCONHR, —CONHSO$_2$R, —NHCONHR, —CH$_2$OR, —CH$_2$CH$_2$OH, alkoxy, substituted alkoxy, aryl, substituted aryl, aryloxy, substituted aryloxy, —CF$_3$, and —OCF$_3$;

R is hydrogen or loweralkyl;

or a pharmaceutically acceptable salt or stereoisomer thereof;

inhibit the tyrosine kinase activity of growth factor receptors such as HER2.

A further embodiment of the invention is illustrated by a compound of Formula I, or a pharmaceutically acceptable salt or stereoisomer thereof, wherein $R^1$ and $R^{1a}$ are independently hydrogen or methyl;

$R^2$ is phenyl, substituted phenyl or piperidine; said substituents on the substituted phenyl group are selected from the group consisting of one or more hydrogen, halogen, alkyl, substituted alkyl, alkoxy, substituted alkoxy and aryloxy;

45$R^3$ is heterocyclyl or substituted heterocyclyl, said substituents on the substituted heterocyclyl group are selected from the group consisting of one or more hydrogen, halogen, —OH, alkyl, substituted alkyl, and —NH$_2$;

A further embodiment of the invention is illustrated by a compound of Formula I, or a pharmaceutically acceptable salt or stereoisomer thereof, wherein $R^1$ and $R^{1a}$ are independently hydrogen or methyl;

$R^2$ is phenyl, substituted phenyl or piperidine; said substituents on the substituted phenyl group are selected from the group consisting of one or more hydrogen, halogen, alkyl, substituted alkyl, alkoxy, substituted alkoxy and aryloxy;

$R^3$ is heterocyclyl or substituted heterocyclyl, said substituents on the substituted heterocyclyl group are selected from the group consisting of one or more hydrogen, halogen, —OH, alkyl, substituted alkyl, and —NH$_2$.

Illustrative compounds of the invention include the following:

5-[(4-aminopiperidin-1-yl)methyl]-N-[(1R)-1-phenylethyl]pyrrolo[2,1-f][1,2,4]triazin-4-amine, BMS-673675

5-[(4-aminopiperidin-1-yl)methyl]-N-(3-chlorobenzyl)pyrrolo[2,1 f][1,2,4]triazin-4-amine, BMS-674686

5-[(4-aminopiperidin-1-yl)methyl]-N-(4-fluorobenzyl)pyrrolo[2,1-f][1,2,4]triazin-4-amine, BMS-674688

5-[(4-aminopiperidin-1-yl)methyl]-N-[(1R)-1-(4-fluorophenyl)ethyl]pyrrolo[2,1-f][1,2,4]triazin-4-amine, BMS-687373 rac-5-[(4-aminopiperidin-1-yl)methyl]-N-(1-phenylethyl)pyrrolo[2,1-f][1,2,4]triazin-4-amine, BMS-691086

5-[(4-aminopiperidin-1-yl)methyl]-N-[(1R)-1-phenylpropyl]pyrrolo-[2,1-f][1,2,4]triazin-4-amine; and BMS-687404

(3R,4R)-4-amino-1-[(4-{[(1R)-1-phenylethyl]amino}pyrrolo[2,1-f][1,2,4]triazin-5-yl)methyl]piperidin-3-ol BMS-720325 or a pharmaceutically acceptable salt, ester, solvate or stereoisomer thereof.

Compounds of the instant invention exhibit IC$_{50}$ values of less than 5 µM in one or more of HER1, HER2 and HER4 assays.

Also included within the scope of the invention is a pharmaceutical composition which comprises at least one compound of formula I as described above and a pharmaceutically acceptable carrier.

Also included is a method for treating proliferative diseases, comprising administering to a mammal in need thereof, a therapeutically effective amount of at least one compound of formula I.

Also included is a method for treating or preventing cancer, comprising administering to a mammal in need thereof, a therapeutically effective amount of at least one compound of formula I.

The following are definitions of terms that may be used in the present specification. The initial definition provided for a group or term herein applies to that group or term throughout the present specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, substituted alkylamino, cycloalkylamino, substituted cycloalkylamino, arylamino, substituted arylamino, aralkylamino, substituted aralkyamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. SO$_2$NH$_2$, substituted sulfonamido, nitro, cyano, carboxy, carbamyl, e.g. CONH$_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl or a substituted aryl group bonded directly through an alkyl group, such as benzyl.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclyl" refer to an optionally substituted, filly saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents.

Also included are smaller heterocyclyls, such as, epoxides and aziridines.

The term "carbocyclic ring" refers to stable, saturated or partially unsaturated monocyclic hydrocarbon rings of 3 to 7 carbon atoms such as cyclopropyl, cyclobutyl, cyclopentyl, cyclohexyl and cycloheptyl. The term "optionally substituted" as it refers to "carbocyclic ring" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy [lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfufric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention includes all the possible stereoisomers and their mixtures. Particularly preferred are the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Any compound that will be converted in vivo to provide the bioactive agent (i.e., the compound for formulas I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, 8, 1–38 (1992);

It should further be understood that solvates (e.g., hydrates) of the compounds of formula I are also with the scope of the present invention. Methods of solvation are generally known in the art.

The present invention is based on the discovery that certain pyrrolotriazine compounds are inhibitors of protein kinases. More specifically, compounds such as those described in this invention, inhibit the protein tyrosine kinase activity of members of the HER family of receptors. These inhibitors will be useful in the treatment of proliferative diseases that are dependent on signaling by one or more of these receptors. Such diseases include psoriasis, rheumatoid arthritis, and solid tumors of the lung, head and neck, breast, colon, ovary, and prostate. The compounds can be formulated in pharmaceutical compositions which are expected to inhibit the growth of those primary and recurrent solid tumors which are associated with HER1 (EGF receptor) and HER2, especially those tumors which are significantly dependent on HER1 or HER2 for their growth and spread, including for example, cancers of the bladder, squamous cell, head, colorectal, esophageal, gynecological (such as ovarian), pancreas, breast, prostate, vulva, skin, brain, genitourinary tract, lymphatic system (such as thyroid), stomach, larynx and lung. In another embodiment, the compounds of the present invention are also useful in the treatment of noncancerous disorders such as psoriasis and rheumatoid arthritis.

Thus according to a further aspect of the invention there is provided the use of at least one compound of the formula I, or a pharmaceutically acceptable salt thereof, in the manufacture of a medicament for use in the production of an antiproliferative effect in a mammalian species such as a human being.

According to a further feature of the invention there is provided a method for producing an antiproliferative effect in a mammalian species, such as a human being, in need of such treatment which comprises administering to said animal an effective amount of at least one compound of formula I or a pharmaceutically acceptable salt thereof as defined herein before.

By virtue of their ability to inhibit HER1, HER2, and HER4 kinases, compounds of the present invention can be used for the treatment of proliferative diseases, including psoriasis and cancer. The HER1 receptor kinase has been shown to be expressed and activated in many solid tumors including head and neck, prostate, non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor efficacy in preclinical and clinical studies. It is therefore expected that inhibitors of the HER1 and HER2 kinases will have efficacy in the treatment of tumors that depend on signaling from either of the two receptors. In addition, these compounds will have efficacy in inhibiting tumors that rely on HER receptor heterodimer signaling. These compounds are expected to have efficacy either as single agent or in combination (simultaneous or sequentially) with other chemotherapeutic agents such as Taxol, adriamycin, and cisplatin. Since HER1 and HER2 signaling has been shown to regulate expression of angiogenic factors such as vascular endothelial growth factor (VEGF) and interleukin 8 (IL8), these compounds are expected to have anti-tumor efficacy resulting from the inhibition of angiogenesis in addition to the inhibition of tumor cell proliferation and survival. The HER2 receptor has been shown to be involved in the hyperproliferation of synovial cells in rheumatoid arthritis, and may contribute to the angiogenic component of that inflammatory disease state. The inhibitors described in this invention are therefore expected to have efficacy in the treatment of rheumatoid arthritis. The ability of these compounds to inhibit HER1 further adds to their use as antiangiogenic agents. See the following documents and references cited therein: Schlessinger J., "Cell signaling by receptor tyrosine kinases", *Cell* 103(2), p. 211–225 (2000); Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", *J. of Clin. Oncol.* 17(9), p. 2639–2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), p. 904–914 (2000); Satoh, K., Kikuchi, S., Sekimata, M., Kabuyama, Y., Homma, M. K., and Homma Y., "Involvement of ErbB-2 in rheumatoid synovial cell growth", *Arthritis Rheum.* 44(2), p. 260–265 (2001).

The antiproliferative treatment defined herein before may be applied as a sole therapy or may involve, in addition to at least one compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments such as radiation therapy. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment, in addition to the antiproliferative treatment defined herein, may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin $\alpha v \beta 3$ function, angiostatin, razoxane);

(ii) cytostatic agents such as antiestrogens (for example, tamoxifen, toremifene, raloxifene, droloxifene, iodoxifene), progestogens (for example megestrol acetate), aromatase inhibitors (for example anastrozole, letrozole, borazole, exemestane), antihormones, antiprogestogens, antiandrogens (for example flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors like marimastat and inhibitors of urokinase plasminogen activator receptor function) and inhibitors of growth factor function, (such growth factors include for example, EGF, FGF, platelet derived growth factor and hepatocyte growth factor such inhibitors include growth factor antibodies, growth factor receptoriantibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotepa; antimitotic agents (for example vinca alkaloids like vincristine and taxoids like Taxol® (paclitaxel), Taxotere® (docetaxel) and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors; biological response modifiers and proteasome inhibitors such as Velcade® (bortezomib).

The compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, and osteosarcoma.

Due to the key role of kinases in the regulation of cellular proliferation in general, kinase inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease The compounds of formula I are especially useful in treatment of tumors having a high incidence of tyrosine kinase activity, such as colon, lung, and pancreatic tumors.

By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as HER1 (EGF receptor), HER2, or HER4.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste, masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.TM. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

BIOLOGICAL ASSAYS

HER1, HER2 or HER4 Kinase Assays

Compounds of interest were assayed in a kinase buffer that contained 20 mM Tris.HCl, pH 7.5, 10 mM $MnCl_2$, 0.5 mM dithiothreitol, bovine serum albumin at 0.1 mg/ml, poly(glu/tyr, 4:1) at 0.1 mg/ml, 1 µM ATP, and 4 µCi/ml [$\gamma$-$^{33}$P]ATP. Poly(glu/tyr, 4:1) is a synthetic polymer that serves as a phosphoryl acceptor and is purchased from Sigma Chemicals. The kinase reaction is initiated by the addition of enzyme and the reaction mixtures were incubated at 26° C. for 1 h. The reaction is terminated by the addition of EDTA to 50 mM and proteins are precipitated by the addition of trichloroacetic acid to 5%. The precipitated proteins are recovered by filtration onto Packard Unifilter plates and the amount of radioactivity incorporated is measured in a Topcount scintillation counter.

For the preparation of recombinant HER1 and HER4, the cytoplasmic sequences of the receptors were expressed in insect cells as GST fusion proteins, which were purified by affinity chromatography. The cytoplasmic sequence of HER2 was subcloned into the baculovirus expression vector pBlueBac4 (Invitrogen) and was expressed as an untagged protein in insect cells. The recombinant protein was partially purified by ion-exchange chromatography.

The instant compounds inhibit HER1, HER2, and HER4 kinases with $IC_{50}$ values between 0.001 and 25 µM. Preferred compounds have $IC_{50}$ values between 0.001–5.0 µM. More preferred compounds have $IC_{50}$ values between 0.001–1.0 µM. Most preferred compounds have $IC_{50}$ values between 0.001–0.1 µM.

A HERG potassium channel assay may be used to screen compounds for

HERG activity (see Caballero R, et al., *Direct Effects of Candesartan and Eprosartan on Human Cloned Potassium Channels Involved in Cardiac Repolarization*, Molecular Pharmacology, Vol. 59, No. 4, pp. 825–36, 2001). Accordingly, preferred compounds have lower HERG assay activity.

METHODS OF PREPARATION

Certain compounds of formula I may generally be prepared according to the following schemes and the knowledge of one skilled in the art. Supplemental preparation information may also be found in co-pending U.S. patent application Ser. No. 09/573,829 filed May 18, 2000 and international applications published under the Patent Cooperation Treaty (PCT), International Publication Number WO 00/71129 and WO 03/042172, all of which are incorporated by reference herein.

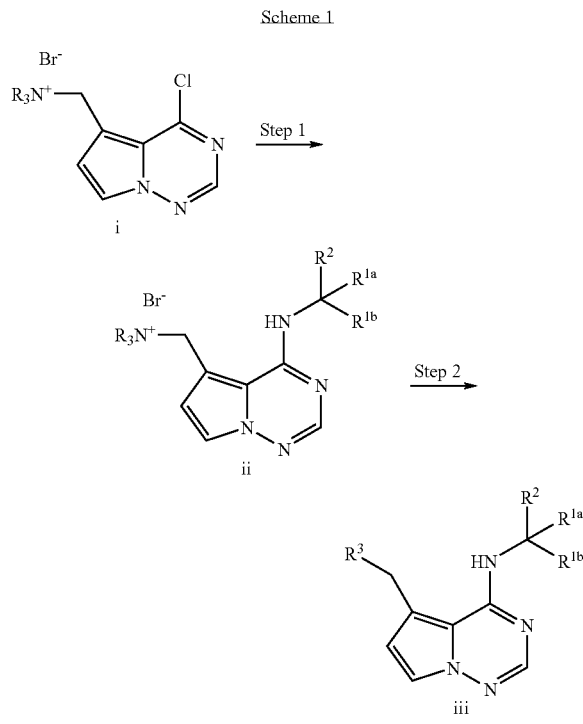

Step 1 The first step of Scheme 1 is accomplished by treating Compound i (Ref. U.S. Ser. No. 60/533,335 filed Dec. 29, 2003) with a benzyl amine, or a substituted benzyl amine, in the presence of a tertiary base such as triethylamine, or diisopropylethylamine, in an anhydrous solvents such as THF, DMF, DMA, acetonitrile or chloroform, at a temperature between about 20° C. to about 120° C., to give an ammonium salt, Compound ii.

Step 2 Compound ii is treated with an amine, or a substituted amine, such as N-Boc-aminopiperidine, in the presence of a tertiary base such as triethylamine, or diisopropylethylamine, in an anhydrous solvents such as THF, DMF, DMA, acetonitrile or chloroform, at temperature between about 20° C. to about 120° C., to give Compound iii.

Compounds prepared by the above methods having general formula iv in Scheme 2 in which the 5-methylsubstituent contains a protecting group such as t-butoxycarbonyl may further be modified by removal of the protecting group in Step 1 by treatment with anhydrous HCl in diethyl ether or 1,4-dioxane or by treatment of a solution of the compound in $CH_2Cl_2$ with trifluoroacetic acid to prepare the free amine v.

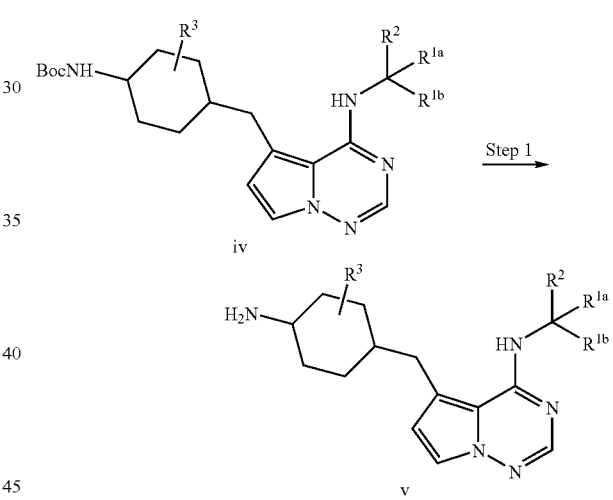

In addition, other compounds of formula I may be prepared using procedures generally known to those skilled in the art. In particular, the following examples provide additional methods for the preparation of the compounds of this invention.

The invention will now be further described by the following working example(s), which are preferred embodiments of the invention. All temperatures are in degrees Celsius (° C.) unless otherwise indicated. "HPLC Ret Time" is the HPLC retention time that was obtained under the following conditions: column type and length, gradient time [unless otherwise indicated, all gradients started with 100% solvent A (10% MeOH, 90% $H_2O$, 0.1% TFA) and ended with 100% solvent B (90% MeOH, 10% $H_2O$, 0.1% TFA)], flow rate (mL/min). UV detection was always conducted at 220 nM. These examples are illustrative rather than limiting and it is to be understood that there may be other embodiments that fall within the spirit and scope of the invention as defined by the claims appended hereto.

EXAMPLE 1

5-[(4-aminopiperidin-1-yl)methyl]-N-[(1R)-1-phenylethyl]pyrrolo[2,1-f][1,2,4]triazin-4-amine (BMS-673675)

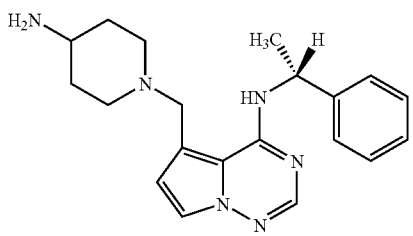

1A. Preparation of (4-chloro-pyrrolo[2,1-f][1,2,4]triazin-5-ylmethyl)-triethyl-ammonium bromide (IA)

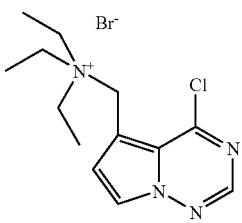

A mixture of 5-(bromomethyl)-4-chloropyrrolo[1,2-f][1,2,4]triazine (2.7 g, 11 mmol)(Ref. WO 03/042172 A2) and Et$_3$N (5 ml, 36 mmol) in THF (20 ml) was stirred at room temperature for 48 hours. The solid was filtered and rinsed with THF and Et$_2$O and dried to give Compound 1A (3.38 g, 89%). The compound had an analytical HPLC retention time=0.78 min. (Chromolith SpeedROD 4.6×50 mm, 10–90% aqueous methanol over 4 minutes containing 0.1% TFA, 4 ml/min, monitoring at 220nm) and a LC/MSM$^+$=267.

Method One:

1B. Preparation of (R)-5-((4-aminopiperidin-1-yl)methyl-N-(1-phenylethyl)pyrrolo-[1,2-f][1,2,4]triazin-4-amine (IB)

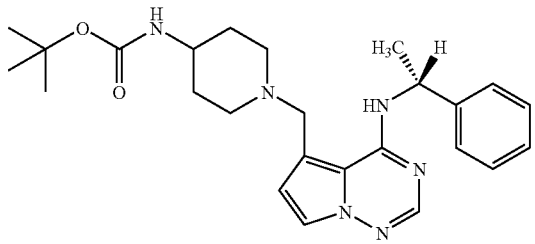

To a mixture of Compound 1A (100 mg, 0.29 mmol) and (R)-1-phenylethanamine (34.9 mg, 0.29 mmol) in 1 mL of DMA was added DIEA (37.2 mg, 0.29 mmol). The mixture was heated at 45° C. for 5 h and at 60° C. for 14 h. The mixture was then cooled to room temperature and diluted with 1 mL of DMA. DIEA (37.2 mg, 0.29 mmol) was added and the mixture was stirred at room temperature for 2 h. The mixture was then mixed with tert-butyl piperidine-4-ylcarbamate (100 mg, 0.50 mmol) and DIEA (74.4 mg, 0.58 mmol), heated at 70° C. for 7 h, and cooled to room temperature. The mixture was diluted with methanol and purified by prep HPLC to give Compound 1B in 37% yield. Compound 1B had an analytical HPLC retention time=2.98 min. (YMC S5 ODS column 4.6×50 mm, 10–90% aqueous methanol over 4 minutes containing 0.2% phosphoric acid, 4 ml/min, monitoring at 220 nm) and a LC/MS M$^+$+1=451.

1C. Preparation of 5-[(4-aminopiperidin-1-yl)methyl]-N-[(1R)-1-phenylethyl]pyrrolo-[2,1-f][1,2,4]triazin-4-amine (IC)

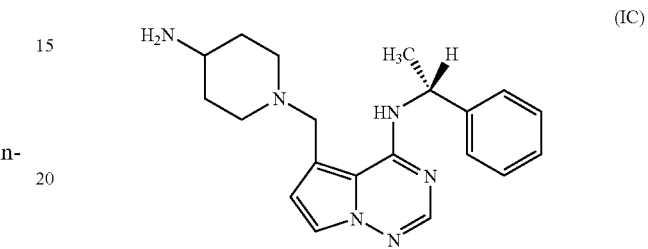

To a stirred solution of 1B (48.9 mg, 0.11 mmol) in 1 mL of DCM at room temperature was added TFA (1.00 mL, 13.0 mmol). The mixture was stirred at room temperature for 15 min and concentrated in vacuo. The residue was purified by prep HPLC to give 1C in 90% yield. It had an analytical HPLC retention time=1.58 min. (YMC S5 ODS column 4.6×50 mm, 10–90% aqueous methanol over 4 minutes containing 0.2% phosphoric acid, 4 ml/min, monitoring at 220 nm) and a LC/MS M$^+$+1=351.

Method Two:

1C. Preparation of 5-[(4-aminopiperidin-1-yl)methyl]-N-[(1R)-1-phenylethyl]pyrrolo-[2,1-f][1,2,4]triazin-4-amine

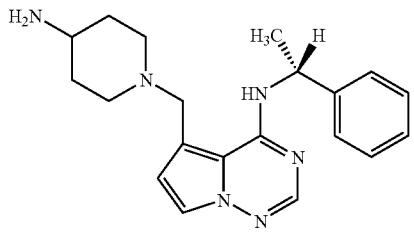

To a mixture of Compound 1A (100 mg, 0.29 mmol) and (R)-1-phenylethanamine (34.9 mg, 0.29 mmol) in 0.6 mL of DMA was added DIEA (37.2 mg, 0.29 mmol). The mixture was stirred at room temperature for 17 h upon which time DIEA (74.4 mg, 0.58 mmol) and tert-butyl piperidine-4-ylcarbamate (86.4 mg, 0.43 mmol) were added. The mixture was heated at 70° C. for 3 h and cooled to room temperature. TFA (2.00 mL, 260 mmol) was added and the mixture was stirred at room temperature for 1 h. The mixture was concentrated in vacuo and the residue was purified by prep HPLC to give Compound 1C in 62% yield. Compound 1C had an analytical HPLC retention time=1.58 min. (YMC S5 ODS column 4.6×50 mm, 10–90% aqueous methanol over 4 minutes containing 0.2% phosphoric acid, 4 ml/min, monitoring at 220 nm) and a LC/MS M$^+$+1=351.

Examples 2 to 27 were similarly prepared utilizing either Method One or Method Two with the corresponding benzyl amines.

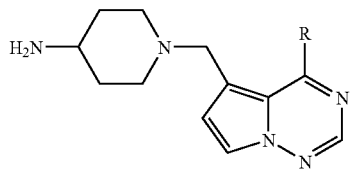

| Ex # | R | Name | [M + H] | HPLC Ret Time (min) |
|---|---|---|---|---|
| 2 | H₃C, phenyl, NH | 5-[(4-aminopiperidin-1-yl)methyl]-N-[(1S)-1-phenylethyl]pyrrolo[2,1-f][1,2,4]triazin-4-amine | 351 | 1.56 |
| 3 | benzyl, NH | 5-[(4-aminopiperidin-1-yl)methyl]-N-benzyl-pyrrolo[2,1-f][1,2,4]triazin-4-amine | 337 | 1.33 |
| 4 | 2-Cl-benzyl, NH | 5-[(4-aminopiperidin-1-yl)methyl]-N-(2-chlorobenzyl)pyrrolo[2,1-f][1,2,4]triazin-4-amine | 371 | 1.65 |
| 5 | 3-Cl-benzyl, NH | 5-[(4-aminopiperidin-1-yl)methyl]-N-(3-chlorobenzyl)pyrrolo[2,1-f][1,2,4]triazin-4-amine | 371 | 1.77 |
| 6 | 4-Cl-benzyl, NH | 5-[(4-aminopiperidin-1-yl)methyl]-N-(4-chlorobenzyl)pyrrolo[2,1-f]-[1,2,4]triazin-4-amine | 371 | 1.78 |
| 7 | 4-F-benzyl, NH | 5-[(4-aminopiperidin-1-yl)methyl]-N-(4-fluorobenzyl)pyrrolo[2,1-f]-[1,2,4]triazin-4-amine | 355 | 1.41 |
| 8 | 4-OPh-benzyl, NH | 5-[(4-aminopiperidin-1-yl)methyl]-N-(4-phenoxybenzyl)pyrrolo-[2,1-f][1,2,4]triazin-4-amine | 429 | 2.51 |
| 9 | H₃C, 4-F-phenyl, NH | 5-[(4-aminopiperidin-1-yl)methyl]-N-[(1R)-1-(4-fluorophenyl)ethyl]pyrrolo[2,1-f][1,2,4]triazin-4-amine | 369 | 1.67 |
| 10 | H₃C, 3-OMe-phenyl, NH | 5-[(4-aminopiperidin-1-yl)methyl]-N-[(1R)-1-(3-methoxyphenyl)ethyl]pyrrolo[2,1-f][1,2,4]triazin-4-amine | 381 | 1.81 |
| 11 | H₃C, 4-OMe-phenyl, NH | 5-[(4-aminopiperidin-1-yl)methyl]-N-[(1R)-1-(4-methoxyphenyl)ethyl]pyrrolo[2,1-f][1,2,4]triazin-4-amine | 381 | 1.75 |

-continued

| Ex # | R | Name | [M + H] | HPLC Ret Time (min) |
|---|---|---|---|---|
| 12 | (1-(4-methylphenyl)ethyl)amino, CH3 | 5-[(4-aminopiperidin-1-yl)methyl]-N-[(1R)-1-(4-methylphenyl)ethyl]pyrrolo[2,1-f][1,2,4]triazin-4-amine | 365 | 1.97 |
| 13 | (1-phenylethyl)amino | rac-5-[(4-aminopiperi-din-1-yl)methyl]-N-(1-phenylethyl)pyrrolo[2,1-f][1,2,4]triazin-4-amine | 351 | 1.55 |
| 14 | (1-(4-fluorophenyl)ethyl)amino | rac-5-[(4-aminopiperi-din-1-yl)methyl]-N-[1-(4-fluorophenyl)ethyl]pyrrolo[2,1-f][1,2,4]triazin-4-amine | 369 | 1.66 |
| 15 | (1-(4-chlorophenyl)ethyl)amino | rac-5-[(4-aminopiperi-din-1-yl)methyl]-N-[1-(4-chlorophenyl)ethyl]pyrrolo[2,1-f][1,2,4]triazin-4-amine | 385 | 2.04 |
| 16 | (1-(4-bromophenyl)ethyl)amino | rac-5-[(4-aminopiperi-din-1-yl)methyl]-N-[1-(4-bromophenyl)ethyl]pyrrolo[2,1-f][1,2,4]triazin-4-amine | 429 | 2.14 |
| 17 | (1-phenylpropyl)amino | 5-[(4-aminopiperidin-1-yl)methyl]-N-[(1R)-1-phenylpropyl]pyrrolo[2,1-f][1,2,4]triazin-4-amine | 365 | 1.90 |
| 18 | (2-hydroxy-1-phenylethyl)amino | (2S)-2-({5-[(4-aminopi-peridin-1-yl)methyl]-pyrrolo[2,1-f][1,2,4]-triazin-4-yl}amino)-2-phenylethanol | 367 | 1.38 |
| 19 | N-benzyl-N-methylamino | 5-[(4-aminopiperidin-1-yl)methyl]-N-benzyl-N-methylpyrrolo[2,1-f][1,2,4]triazin-4-amine | 351 | 1.44 |
| 20 | N-methyl-N-(1-phenylethyl)amino | 5-[(4-aminopiperidin-1-yl)methyl]-N-methyl-N-[(1R)-1-phenylethyl]-pyrrolo[2,1-f][1,2,4]tria-zin-4-amine | 365 | 1.62 |

-continued

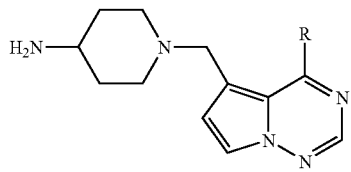

| Ex # | R | Name | [M + H] | HPLC Ret Time (min) |
|---|---|---|---|---|
| 21 | (diphenylmethyl-NH-) | 5-[(4-aminopiperidin-1-yl)methyl]-N-(diphenyl-methyl)pyrrolo[2,1-f][1,2,4]triazin-4-amine | 413 | 2.23 |
| 22 | H₃C-CH(NH-)-(pyridin-2-yl) | rac-5-[(4-aminopiperi-din-1-yl)methyl]-N-(1-pyridin-2-ylethyl)-pyrrolo[2,1-f][1,2,4]-triazin-4-amine | 352 | 0.32 |
| 23 | H₃C-CH(NH-)-(pyridin-3-yl) | rac-5-[(4-aminopiperi-din-1-yl)methyl]-N-(1-pyridin-3-ylethyl)-pyrrolo[2,1-f][1,2,4]-triazin-4-amine | 352 | 0.61 |
| 24 | H₃C-CH(NH-)-(pyridin-4-yl) | rac-5-[(4-amino-piperi-din-1-yl)methyl]-N-(1-pyridin-4-ylethyl)-pyrrolo[2,1-f][1,2,4]-triazin-4-amine | 352 | 0.56 |

EXAMPLE 25

25A. Preparation of (S)-1-(2-nitrophenylsulfonyl)-4-((4-((R)-1-phenylethylamino)-pyrrolo[1,2-f][1,2,4]triazin-5-yl)-1,4-diazepan-6-ol

25A

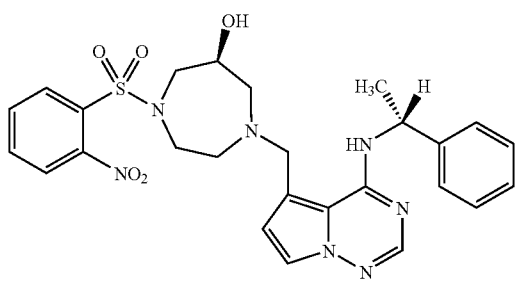

To a mixture of Compound 1A (118 mg, 0.34 mmol) and (R)-1-phenylethanamine (41.4 mg, 0.34 mmol) in 1 mL of DMA was added DIEA (59.5 uL, 0.34 mmol). The mixture was stirred at room temperature for 18.5 h and heated at 45° C. for 1.5 h. The mixture was cooled to room temperature and mixed with Compound 1D (127 mg, 37.6 mmol, ref. U.S. Ser. No. 10/294,281) and DIEA (0.20 mL, 11.5 mmol), and then heated at 70° C. for 18 h. After cooling to room temperature, the mixture was diluted with 80 mL of EtOAc, and washed with water (2×100 mL) and brine (1×60 mL). The organic layer was dried ($MgSO_4$), filtered and concentrated in vacuo to give 141 mg of Compound 25A in 75% yield. The compound had an analytical HPLC retention time=3.36 min. (Phenomenox S5 C18-HC 4.6×50 mm column, 10–90% aqueous methanol over 4 minutes containing 0.1% TFA, 4 ml/min, monitoring at 220 nm) and a LC/MS $M^+$+1=552.

25B. Preparation of (R)-1-((4-((R)-1-phenylethylamino)pyrrolo[1,2-f][1,2,4]triazin-5-yl)-1,4-diazepan-6-ol

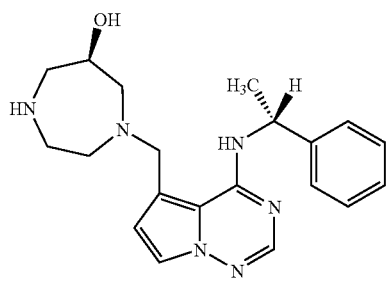

To a stirred mixture of Compound 25A (141 mg, 0.26 mmol) in 1 mL of DMF was added DBU (0.20 mL, 1.34 mmol) and 2-mercaptoethanol (0.10 mL, 1.43 mmol). The reaction mixture was stirred at room temperature for 30 min. The mixture was purified by prep HPLC to give 57 mg of desired Compound 25B in 60% yield. The compound had an analytical HPLC retention time=1.47 min. (YMC S5 ODS column 4.6×50 mm, 10–90% aqueous methanol over 4 minutes containing 0.2% phosphoric acid, 4 ml/min, monitoring at 220 nm) and a LC/MS $M^++1=367$.

EXAMPLE 26

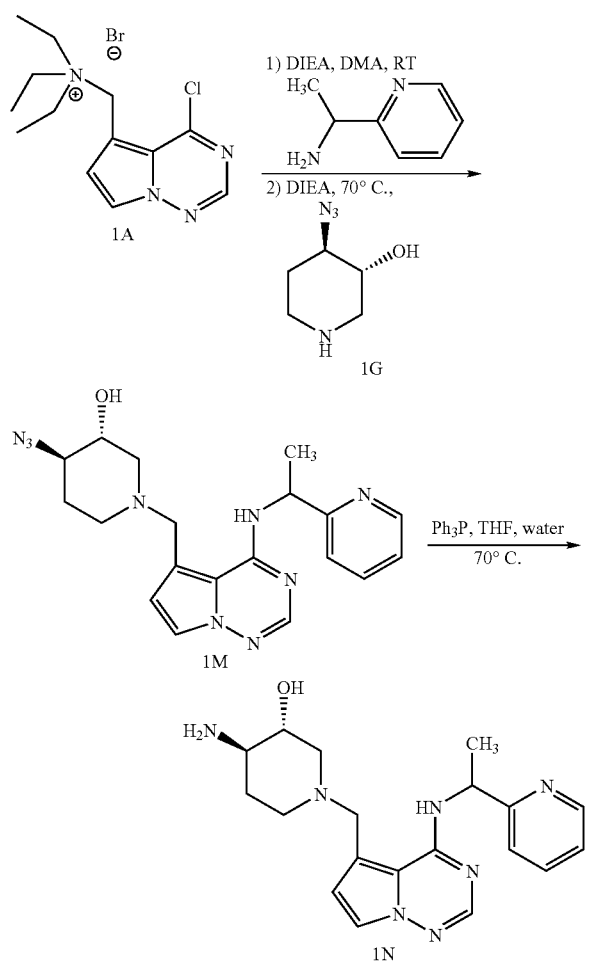

26A. Preparation of (3R,4R)-4-azido-1-((4-(1-(pyridine-2-yl)ethylamino)pyrrolo[1,2-f][1,2,4]triazin-5-yl)methyl)piperidin-3-ol

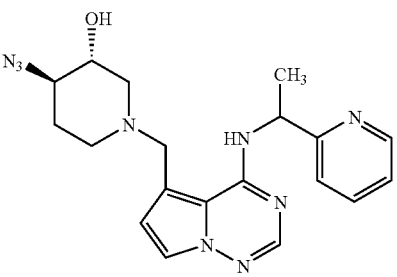

To a mixture of 1A (200 mg, 0.58 mmol) and (1-pyridin-2-yl)ethanamine (70.2 mg, 0.58 mmol; ref.: Inorganic Syntheses, 32, 1998, p 70–75) in 2 mL of DMA was added DIEA (100 uL, 0.58 mmol). The mixture was stirred at room temperature for 40 h upon which time DIEA (300 uL, 0.87 mmol) and (3R,4R)-4-azidopiperidin-3-ol (100 mg, 0.70 mmol; ref. U.S. Ser. No. 60/533,335) were added. The mixture was heated at 70° C. for 23 h and was cooled to room temperature. The mixture was diluted with 100 mL of EtOAc and washed with water (2×100 mL), saturated NaHCO$_3$ solution (1×40 mL) and brine (1×30 mL). The EtOAc layer was dried (MgSO$_4$), filtered and concentrated in vacuo to give 192 mg of Compound 26A in 85% yield. The compound had an analytical HPLC retention time=1.09 min. (YMC S5 ODS column 4.6×50 mm, 10–90% aqueous methanol over 4 minutes containing 0.2% phosphoric acid, 4 ml/min, monitoring at 220 nm) and a LC/MS $M^++1=394$.

26B. Preparation of (3R,4R)-4-amino-1-((4-(1-(pyridin-2-yl)ethylamino)pyrrolo[1,2-f][1,2,4]triazin-5-yl)methyl)piperidin-3-ol

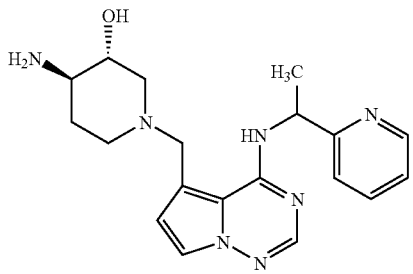

To a stirred mixture of Compound 26A (192 mg, 0.49 mmol) in 2 mL of THF and 0.2 mL of water was added Ph$_3$P (166 mg, 0.63 mmol). The mixture was heated at 70° C. for 4 h and cooled to room temperature. The mixture was divided into two portions and each portion was loaded unto a 2 g SCX cartridge, eluted with MeOH, then with 2M NH$_3$ in MeOH. The combined NH$_3$ in MeOH eluants were concentrated in vacuo to give the crude amine. The amine was diluted with MeOH and purified by prep HPLC to give 164 mg of Compound 26B in 91% yield. The compound had an analytical HPLC retention time=0.88 min. (YMC S5 ODS column 4.6×50 mm, 10–90% aqueous methanol over 4 minutes containing 0.2% phosphoric acid, 4 ml/min, monitoring at 220 nm) and a LC/MS $M^++1=368$.

Examples 27 to 35 were similarly prepared as example 26 utilizing the corresponding amines.

| # | R₁ | R₂ | Name | M + H | HPLC Ret. Time (min) |
|---|----|----|------|-------|---------------------|
| 27 | (R)-CH(CH₃)-NH- phenyl | 6-hydroxy-1,4-diazepan-1-yl (6R) | (6R)-1-[(4-{[(1R)-1-phenylethyl]amino}pyrrolo[2,1-f][1,2,4]triazin-5-yl)methyl]-1,4-diazepan-6-ol | 367 | 1.47 |
| 28 | (R)-CH(CH₃)-NH- pyridin-2-yl, Enantiomer A | (3R,4R)-4-amino-3-hydroxypiperidin-1-yl | (3R,4R)-4-amino-1-[(4-{[(1R)-1-pyridin-2-ylethyl]amino}pyrrolo[2,1-f][1,2,4]triazin-5-yl)methyl]piperidin-3-ol | 368 | 0.53 |
| 29 | (S)-CH(CH₃)-NH- pyridin-2-yl, Enantiomer B | (3R,4R)-4-amino-3-hydroxypiperidin-1-yl | (3R,4R)-4-amino-1-[(4-{[(1S)-1-pyridin-2-ylethyl]amino}pyrrolo[2,1-f][1,2,4]triazin-5-yl)methyl]piperidin-3-ol | 368 | 0.57 |
| 30 | (R)-CH(CH₃)-NH- pyridin-3-yl, Enantiomer A | (3R,4R)-4-amino-3-hydroxypiperidin-1-yl | (3R,4R)-4-amino-1-[(4-{[(1R)-1-pyridin-3-ylethyl]amino}pyrrolo[2,1-f][1,2,4]triazin-5-yl)methyl]piperidin-3-ol | 368 | 0.69 |
| 31 | (S)-CH(CH₃)-NH- pyridin-3-yl, Enantiomer B | (3R,4R)-4-amino-3-hydroxypiperidin-1-yl | (3R,4R)-4-amino-1-[(4-{[(1S)-1-pyridin-3-ylethyl]amino}pyrrolo[2,1-f][1,2,4]triazin-5-yl)methyl]piperidin-3-ol | 368 | 0.69 |
| 32 | (R)-CH(CH₃)-NH- pyridin-4-yl, Enantiomer A | (3R,4R)-4-amino-3-hydroxypiperidin-1-yl | (3R,4R)-4-amino-1-[(4-{[(1R)-1-pyridin-4-ylethyl]amino}pyrrolo[2,1-f][1,2,4]triazin-5-yl)methyl]piperidin-3-ol | 368 | 0.22 |
| 33 | (S)-CH(CH₃)-NH- pyridin-4-yl, Enantiomer B | (3R,4R)-4-amino-3-hydroxypiperidin-1-yl | (3R,4R)-4-amino-1-[(4-{[(1S)-1-pyridin-4-ylethyl]amino}pyrrolo[2,1-f][1,2,4]triazin-5-yl)methyl]piperidin-3-ol | 368 | 0.22 |

-continued

| # | R$_1$ | R$_2$ | Name | M + H | HPLC Ret. Time (min) |
|---|---|---|---|---|---|
| 34 | (1R)-1-phenylethylamino | (3R,4R)-4-amino-3-hydroxypiperidin-1-yl | (3R,4R)-4-amino-1-[(4-{[(1R)-1-phenylethyl-]amino}pyrrolo[2,1-f][1,2,4]triazin-5-yl)methyl]-piperidin-3-ol | 367 | 1.44 |
| 35 | (1S)-1-phenylethylamino | (3R,4R)-4-amino-3-hydroxypiperidin-1-yl | (3R,4R)-4-amino-1-[(4-{[(1S)-1-phenylethyl-]amino}pyrrolo[2,1-f][1,2,4]triazin-5-yl)methyl]-piperidin-3-ol | 367 | 1.50 |

EXAMPLE 36

(3R,4R)-4-amino-1-((4-(2-phenylpropan-2-ylamino)pyrrolo[1,2-f][1,2,4]triazin-5-yl)methyl) piperidin-3-ol

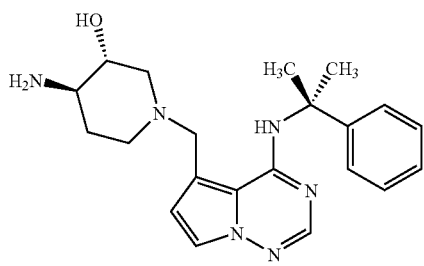

A mixture of 1A (140 mg, 0.4 mmol) and cumylamine (54 mg, 0.4 mmol) in acetonitrile (2 mL) was stirred at RT for 24 h. (3R,4R)-4-azidopiperidine-3-ol (71 mg, 0.5 mmol; ref.: U.S. Ser. No. 60/533,335) and TEA (0.11 mL, 0.8 mmol) were then added. The mixture was heated at 65° C. for 2 h and cooled to room temperature. The mixture was concentrated in vacuo and the residue was purified by prep HPLC. The desired fraction was concentrated, basified with saturated aqueous NaHCO$_3$ solution and extracted with EtOAc. The extract was concentrated and the residue was dissolved in 2 mL of THF and 0.2 ml of water, to which PPh$_3$ (210 mg, 0.8 mmol) was added. The mixture was heated at 70° C. for 2 h and concentrated after cooled to RT. 2 N HCl (2 ml) was added and the mixture was washed with chloroform (×2). The aqueous layer was then basified with 5 N NaOH to pH=11, extracted with EtOAc (×2) and the combined extracts were dried (MgSO$_4$), filtered and concentrated in vacuo. The residue was purified by silica gel column chromatography to give Compound 36 (2.2 mg, 1.4%). The compound has an analytical HPLC retention time=1.50 min (Chromolith SpeedROD 4.6×50 mm, 10–90% aqueous methanol over 4 minutes containing 0.1% TFA, 4 ml/min, monitoring at 220 nm) and a LC/MS M$^+$+1=381.

Numerous modifications and variations of the present invention are possible in light of the above teachings. It is therefore to be understood that within the scope of the appended claims, the invention may be practiced otherwise than as specifically described herein.

What is claimed is:

1. A compound of formula I

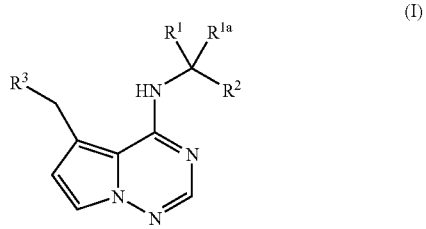

wherein

R$^1$ and R$^{1a}$ are independently hydrogen, loweralkyl or phenyl;

R$^2$ is aryl, substituted aryl, heteroaryl or substituted heteroaryl; said substituents on the substituted aryl or substituted heteroaryl group are selected from the group consisting of one or more hydrogen, halogen, alkyl, substituted alkyl, alkoxy, substituted alkoxy, aryl, substituted aryl, aryloxy and substituted aryloxy;

R³ is heterocyclyl or substituted heterocyclyl, said substituents on the substituted heterocyclyl group are selected from the group consisting of one or more hydrogen, halogen, —OH, alkyl, substituted alkyl, —CN, —NH$_2$, —CONHR, —OCONHR, —CONHSO$_2$R, —NHCONHR, —CH$_2$OR, —CH$_2$CH$_2$OH, alkoxy, substituted alkoxy, aryl, substituted aryl, aryloxy, substituted aryloxy, —CF$_3$, and —OCF$_3$;

R is hydrogen or loweralkyl;

or a pharmaceutically acceptable salt or stereoisomer thereof.

2. The compound as defined in claim 1 wherein

R¹ and R¹ª are independently hydrogen or methyl;

R² is phenyl, substituted phenyl or piperidine; said substituents on the substituted phenyl group are selected from the group consisting of one or more hydrogen, halogen, alkyl, substituted alkyl, alkoxy, substituted alkoxy and aryloxy;

R³ is heterocyclyl or substituted heterocyclyl, said substituents on the substituted heterocyclyl group are selected from the group consisting of one or more hydrogen, halogen, —OH, alkyl, substituted alkyl, and —NH$_2$;

or a pharmaceutically acceptable salt or stereoisomer thereof.

3. The compound as defined in claim 1 wherein

R¹ and R¹ª are independently hydrogen or methyl;

R² is phenyl, substituted phenyl or piperidine; said substituents on the substituted phenyl group are selected from the group consisting of one or more hydrogen, halogen, alkyl, substituted alkyl, alkoxy, substituted alkoxy and aryloxy;

R³ is heterocyclyl or substituted heterocyclyl, said substitutents on the substituted heterocyclyl group are selected from the group consisting of one or more hydrogen, halogen, —OH, alkyl, substituted alkyl, and —NH$_2$;

or a pharmaceutically acceptable salt or stereoisomer thereof.

4. The compound which is

5-[(4-aminopiperidin-1-yl)methyl]-N-[(1R)-1-phenylethyl]pyrrolo[2,1-f][1,2,4]triazin-4-amine, 5-[(4-aminopiperidin-1-yl)methyl]-N-(3-chlorobenzyl)pyrrolo[2,1-f][1,2,4]triazin-4-amine, 5-[(4-aminopiperidin-1-yl)methyl]-N-(4-fluorobenzyl)pyrrolo[2,1-f][1,2,4]triazin-4-amine, 5-[(4-aminopiperidin-1-yl)methyl]-N-[(1R)-1-(4-fluorophenyl)ethyl]pyrrolo[2,1-f][1,2,4]triazin-4-amine, rac-5-[(4-aminopiperidin-1-yl)methyl]-N-(1-phenylethyl)pyrrolo[2,1-f][1,2,4]triazin-4-amine, 5-[(4-aminopiperidin-1-yl)methyl]-N-[(1R)-1-phenylpropyl]pyrrolo-[2,1-f][1,2,4]triazin-4-amine; and (3R,4R)-4-amino-1-[(4-{[(1R)-1-phenylethyl]amino}pyrrolo[2,1-f][1,2,4]triazin-5-yl)methyl]piperidin-3-ol, or a pharmaceutically acceptable salt or stereoisomer thereof.

5. A pharmaceutical composition comprising one or more compound as defined in claim 1 and a pharmaceutically acceptable carrier.

* * * * *